US011963912B2

(12) United States Patent
Lewold

(10) Patent No.: US 11,963,912 B2
(45) Date of Patent: Apr. 23, 2024

(54) SYSTEM FOR POSITIONING AND RESTRAINING AT LEAST A PART OF A HAND

(71) Applicant: ManuFix Scandinavia AB, Bjärred (SE)

(72) Inventor: Stefan Lewold, Bjarred (SE)

(73) Assignee: ManuFix Scandinavia AB, Bjärred (SE)

(*) Notice: Subject to any disclaimer, the term of this patent is extended or adjusted under 35 U.S.C. 154(b) by 96 days.

(21) Appl. No.: 17/296,013

(22) PCT Filed: Oct. 9, 2019

(86) PCT No.: PCT/SE2019/050987
§ 371 (c)(1),
(2) Date: May 21, 2021

(87) PCT Pub. No.: WO2020/106196
PCT Pub. Date: May 28, 2020

(65) Prior Publication Data
US 2022/0087888 A1    Mar. 24, 2022

(30) Foreign Application Priority Data
Nov. 22, 2018   (SE) .................................. 1851443-0

(51) Int. Cl.
*A61G 13/12* (2006.01)
*A61F 5/01* (2006.01)
(Continued)

(52) U.S. Cl.
CPC .......... *A61G 13/124* (2013.01); *A61F 5/0118* (2013.01); *A61G 13/0045* (2016.11); *A61F 5/37* (2013.01); *E05B 75/00* (2013.01)

(58) Field of Classification Search
CPC ......... A61B 46/00; A61B 17/02; A63B 23/00; A63B 23/035; A63B 23/12; A63B 23/16;
(Continued)

(56) References Cited

U.S. PATENT DOCUMENTS 4,204,533 A    5/1980 Forster et al.
5,140,998 A    8/1992 Vickers
(Continued)

FOREIGN PATENT DOCUMENTS

GB   2472380          2/2011
KR   101855359 B1  *  6/2018  ........... A61H 1/0218
WO   0032111          6/2000

OTHER PUBLICATIONS

Machine translation of Publication No. KR101855359 created Jul. 25, 2023 from Espacenet.com (Year: 2018).*
(Continued)

*Primary Examiner* — Ophelia A Hawthorne
*Assistant Examiner* — Gina McCarthy
(74) *Attorney, Agent, or Firm* — Renner, Otto, Boisselle & Sklar, LLP

(57) ABSTRACT

A system for positioning and restraining a hand during hand surgery and similar may include a support plate and a plurality of finger restraining elements, wherein each of the finger restraining elements is removably connectable to a finger or a plurality of fingers, and is detachably attachable to the support plate. The support plate may include a magnetic material, and each of the finger re-straining elements may include a rigid ring portion for receiving a finger, and a fastening portion with a permanent magnet for detachably attaching the finger restraining element in a desired position on the support plate, so that a finger received in the ring portion can be secured to the support plate in the desired position.

16 Claims, 5 Drawing Sheets

Figure 1:
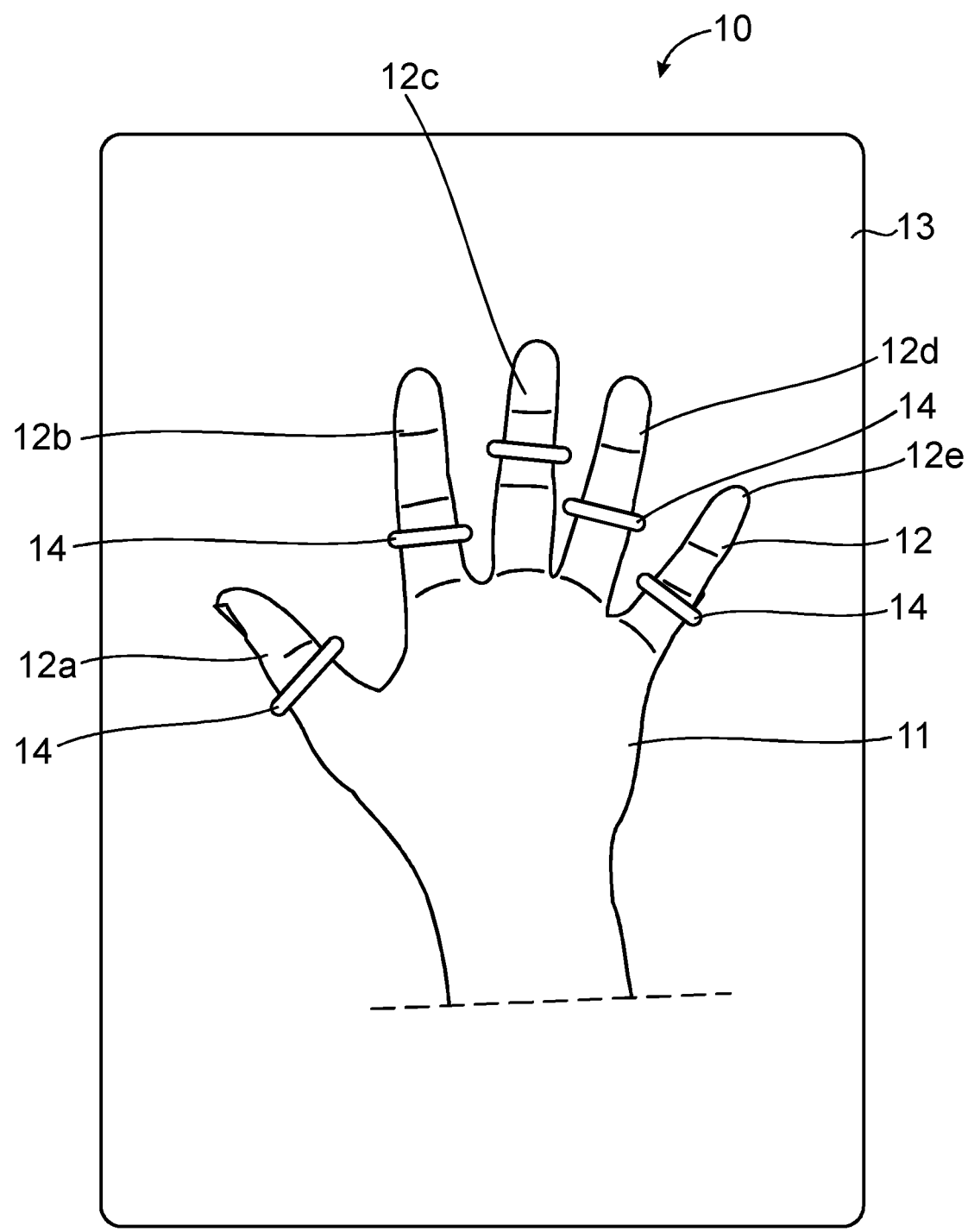

(51) Int. Cl.
*A61F 5/37* (2006.01)
*A61G 13/00* (2006.01)
*E05B 75/00* (2006.01)

(58) Field of Classification Search
CPC .............. A63B 21/4019; A41D 19/00; A41D 19/01582; A41D 19/01588; A61F 5/00; A61F 5/01; A61F 5/0102; A61F 5/0104; A61F 5/013; A61F 5/0118; A61F 5/04; A61F 5/05; A61F 5/058; A61G 13/00; A61G 13/0036; A61G 13/0045; A61G 13/10; A61G 13/12; A61G 13/1205; A61G 13/124; A61G 13/107; E05B 75/00; G10D 3/173; A61H 1/0218
See application file for complete search history.

(56) References Cited

U.S. PATENT DOCUMENTS

| | | | | |
|---|---|---|---|---|
| 6,824,511 | B1 * | 11/2004 | Bell | A61B 17/02 600/227 |
| 7,887,462 | B1 * | 2/2011 | Bearden | A63B 21/4019 2/160 |
| 2006/0272979 | A1 * | 12/2006 | Lubbers | A61B 17/02 206/557 |
| 2015/0075352 | A1 * | 3/2015 | McDonald | G10D 3/173 84/322 |
| 2016/0158082 | A1 * | 6/2016 | Gainor | A61G 13/107 5/690 |

OTHER PUBLICATIONS

T, Anthony, Finger-Friendly Design: Ideal Mobile Touchscreen Target Sizes, Feb. 21, 2012 [online], retrieved on Dec. 7, 2022]. Retrieved from the Internet ,URL: https://www.smashingmagazine.com/2012/02/finger-friendly-design-ideal-mobile-touchscreen-target-sizes/ (Year: 2012).*

Machine translation of Publication No. KR101855359B1 created Jul. 25, 2023 from Espacenet.com (Year: 2018).*

Ring Size? How to Work It Out, In Secret . . . 2023 [online], [retrieved on Jul. 24, 2023]. Retrieved from the Internet <URL:https://violetgraydesign.com/ring-size-guide/ (Year: 2023).*

* cited by examiner

SYSTEM FOR POSITIONING AND RESTRAINING AT LEAST A PART OF A HAND

This application is a national phase of International Application No. PCT/SE2019/050987 filed Oct. 9, 2019, which claims priority to Sweden Patent Application No. 1851443-0 filed Nov. 22, 2018, the entire disclosures of which are hereby incorporated by reference.

FIELD OF THE INVENTION

The invention relates to a system for positioning and restraining at least a part of a hand. More specifically, the invention relates to a system for positioning and restraining at least a part of a hand, such as one or more fingers of a hand, comprising a support plate and a plurality of finger restraining elements, wherein each of the finger restraining elements is removably connectable to a single finger or a plurality of fingers, and is detachably attachable to the support plate. This type of systems is used for positioning and restraining a hand or a part thereof during surgical operations, so that the hand is secured in a desired position during the surgical operation. Hence, such systems are used within health care, such as in hospitals and clinics, for temporarily fixing the hand of a patient during a medical activity, such as hand surgery.

PRIOR ART

There are several different types of medical systems and devices for restraining a hand in the prior art. One such type of prior art system is a hand-shaped plate with strips of a malleable material, wherein the hand of a patient can be positioned on the plate and the strips can be bent over the wrist and fingers to secure the hand to the plate.

There is a need to further improve such systems for restraining a hand according to the prior art.

One problem with such systems for restraining a hand according to the prior art is that it is difficult to position the hand in the desired position. Further, such prior art systems lack in flexibility for restraining hands of different size and shape.

Another problem with such prior art systems is that they tend to break, e.g. from fatigue. Hence, such prior art systems have a limited durability and has low cost efficiency.

SUMMARY OF THE INVENTION

An object of the present invention is to provide an improved system for restraining at least a part of a hand, such as during hand surgery and similar. The present invention makes it possible to provide a flexible and durable system for positioning and securing the hand in a favorable position for different types of surgical operations.

The present invention relates to a system for positioning and restraining at least a part of a hand, comprising a support plate and a plurality of finger restraining elements, wherein each of the finger restraining elements is removably connectable to a finger or a plurality of fingers, and is detachably attachable to the support plate, characterised in that the support plate comprises a magnetic material, and that each of the finger restraining elements comprises at least one rigid ring portion for receiving a finger, and a fastening portion with a permanent magnet for attaching the finger restraining element to the support plate, so that a finger received in the ring portion is secured to the support plate in a desired position. The combination of rigid ring portions for connection to the fingers and the permanent magnet of the fastening portions interacting with the magnetic support plate results in that the fingers can be positioned in the desired positions on the support plate and held in said desired position by means of magnetism. The system according to the invention can allow easy repositioning of one or more fingers and/or the hand. For example, one or more fingers and/or the hand can easily be repositioned while still being connected to the support plate. Also, one or more fingers and/or the hand can easily be repositioned while still fixating the remaining fingers or the hand. Hence, one or more fingers and/or the hand can easily be repositioned while unintentional displacement of the hand or fingers can be prevented. For example, the finger restraining elements can be manually and individually displaced along a plane of the support plate while remaining engaged therewith due to the permanent magnet of the fastening portion.

Further, the present invention makes it possible to provide a durable and cost-efficient system for positioning and restraining a hand during hand surgery. Also, the rigid ring portions make it possible to provide reliable and comfortable restraining during long periods of time without obstructing blood flow to the fingers. Together with the possibilities of easy repositioning of the finger retraining elements, such as turning or moving, any detected blood flow obstruction can be easily remedied. For example, an inner diameter of the ring portion can be selected to provide a relatively loose fit on a single finger, such as 18-28 mm or 22-26 mm for one set and 18-22 mm for another set. The opening of the ring portion can be substantially circular.

The fastening portion can comprise a casing at least partially enclosing the permanent magnet, such as around a periphery of the permanent magnet between a top side and a bottom side thereof. leaving the bottom side of the permanent magnet unobstructed by the casing. The casing can be formed in a magnetic material, e.g. including iron. Hence, a magnet system ca be achieved, wherein the magnetic field is amplified and focused in a direction away from the ring portion and toward the support plate, which direction generally is downward.

The fastening portion can comprise a cover for entirely covering the magnet and, if applicable, also the casing. Hence, the magnet is protected by the cover, for increased durability. Also, the cover can provide a surface of the fastening portion that is easy to sterilize.

The permanent magnet can be a neodymium magnet or other high temperature resistant magnet tolerating an operational temperature of at least 120 degrees, so that the finger restraining element can be sterilized by heat, such as by means of a conventional autoclave, without irreversibly being demagnetized.

The support plate can be covered by a removable surgical drape, such as a conventional surgical drape, wherein the support plate can be protected during use and can be reusable without sterilization.

The system can comprise a plurality of finger restraining elements with ring portions having different inner diameters to fit a variety of different hand sizes and finger sizes. Hence, the system can comprise a plurality of sets of finger restraining elements of different sizes. The finger restraining elements can be adapted to receive and hold a single finger. Alternatively, the finger restraining elements can be adapted to receive and hold a plurality of fingers, such as two or even three fingers. For example, a finger restraining element can comprise a single ring portion or a plurality of ring portions.

The ring portion can be permanently fixed to the fastening portion.

Hence, a finger restraining element in a single piece without moving parts or detachable parts is achieved which makes it easy to operate and clean. Alternatively, the ring portion can be detachably connectable to the fastening portion, such as by conventional mechanical fastening means. Hence, a module system can be achieved, wherein a single fastening portion can be used for different ring portions, e.g. having different sizes to fit fingers of different sizes, so that a ring portion of a suitable size can be selected and mounted on the fastening portion. In such a case the system can comprise a smaller number of fastening portions than ring portions, which results in further cost savings while maintaining a highly flexible system.

Further characteristics and advantages of the present invention will become apparent from the description of the embodiments below, the appended drawings and the dependent claims.

SHORT DESCRIPTION OF THE DRAWINGS

Figure 2:
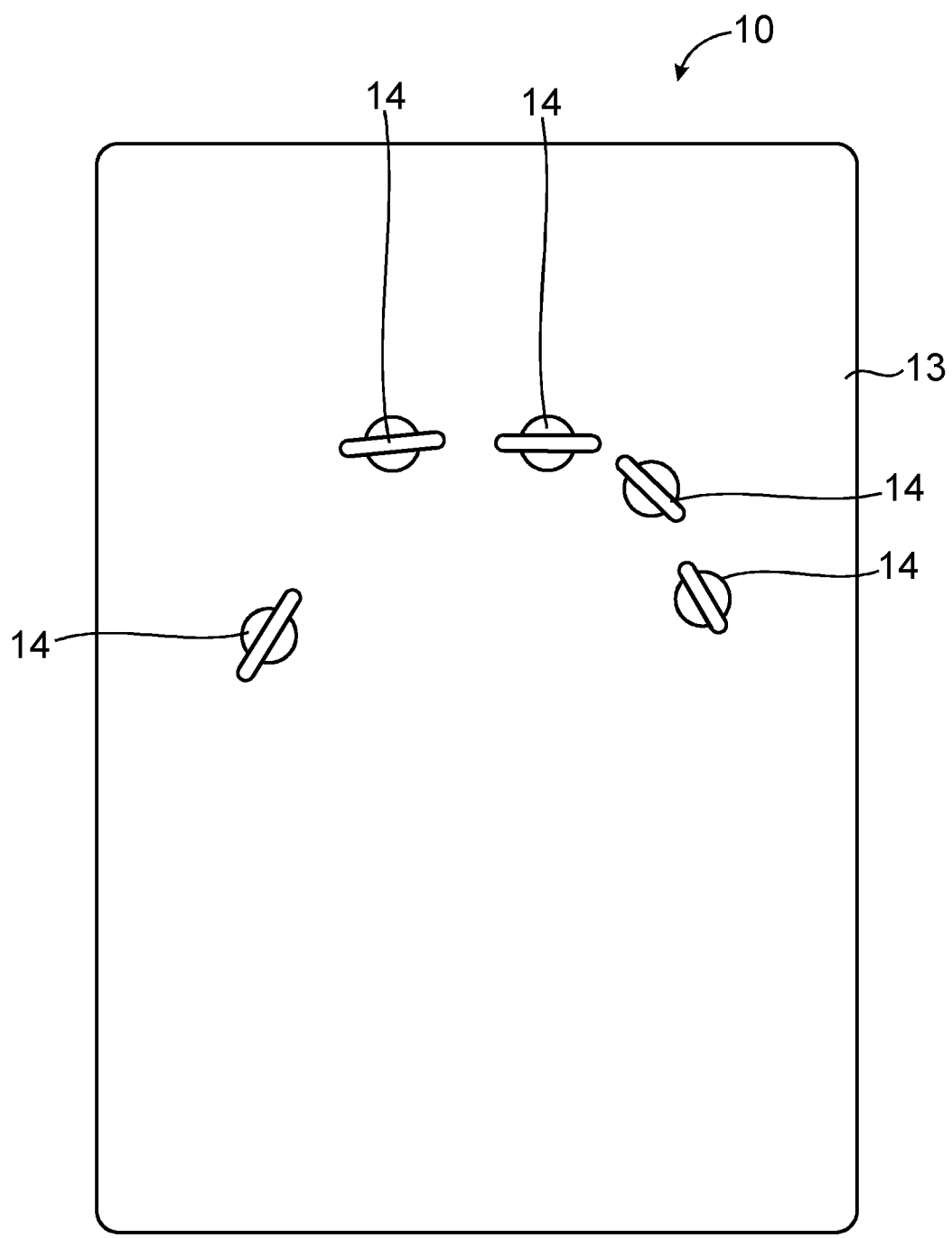
Figure 3:
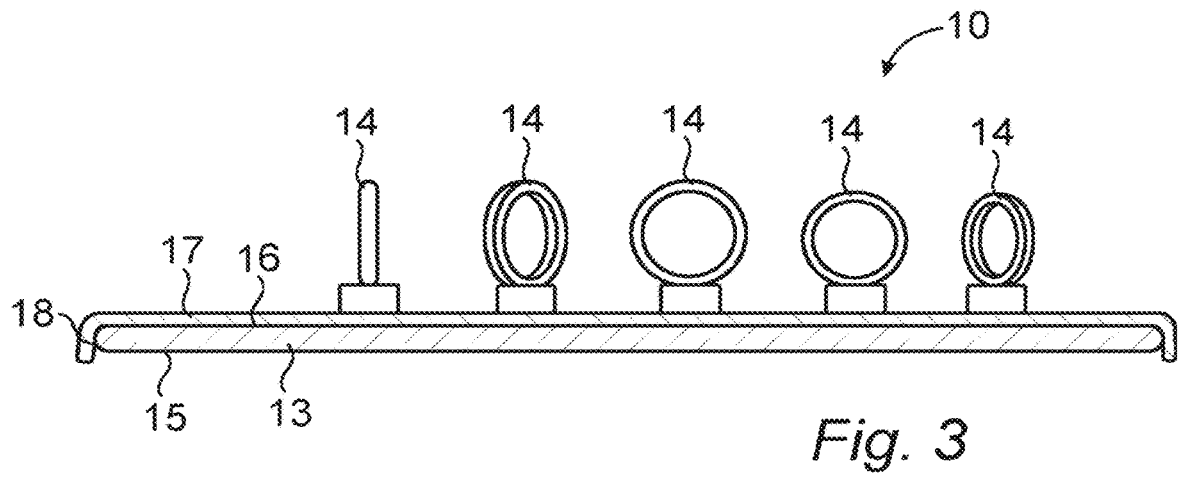
Figure 4:
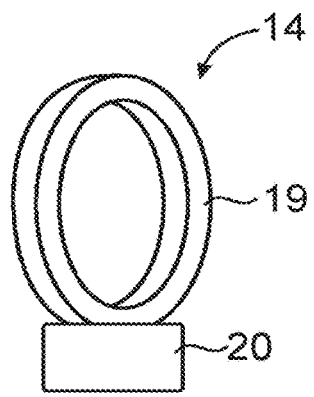
Figure 5:
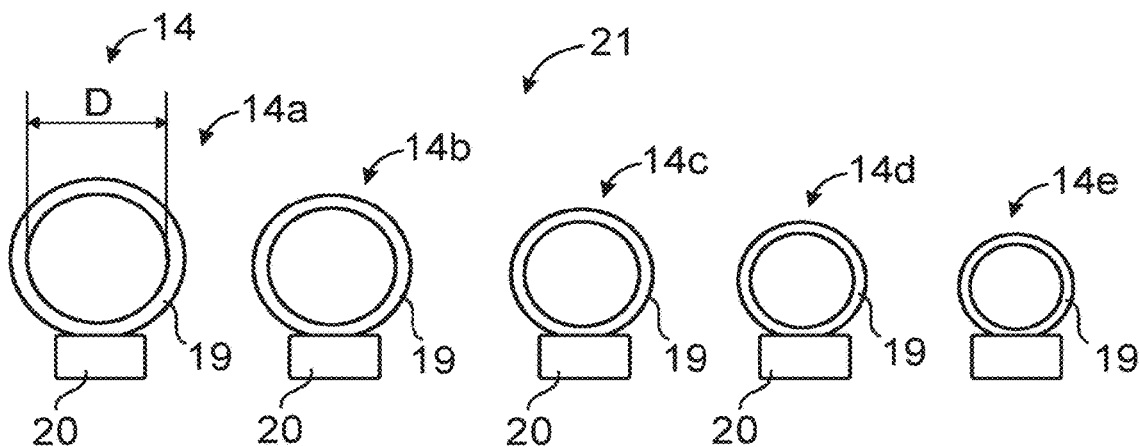
Figure 6:
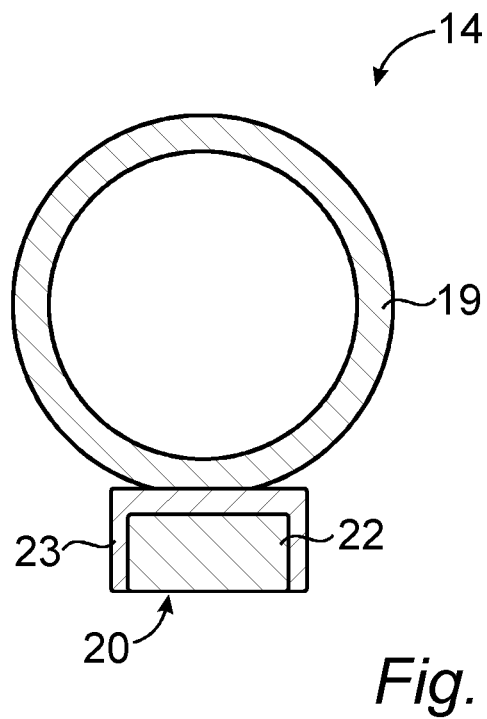
Figure 7:
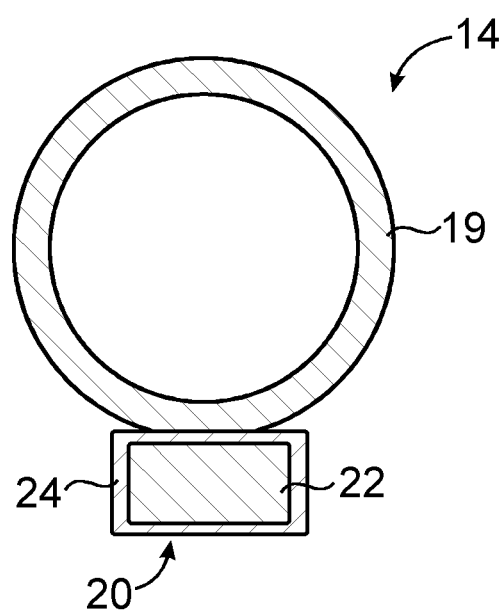
Figure 8:
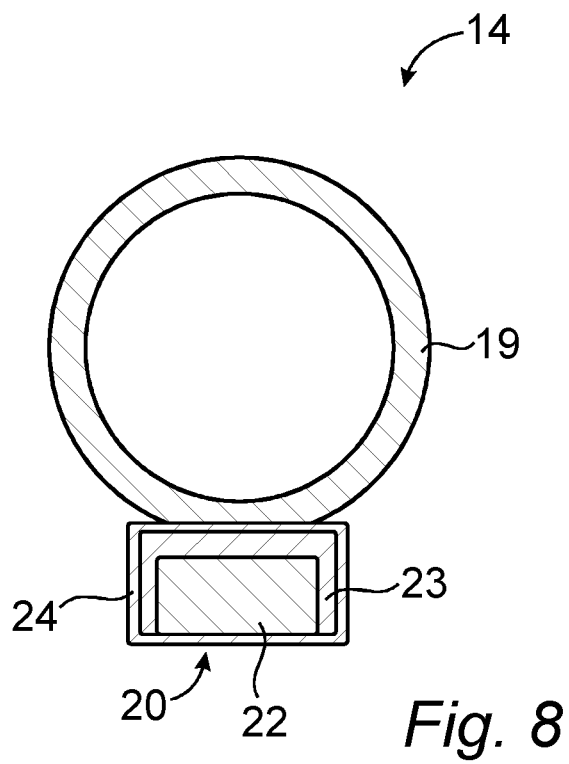
Figure 9:
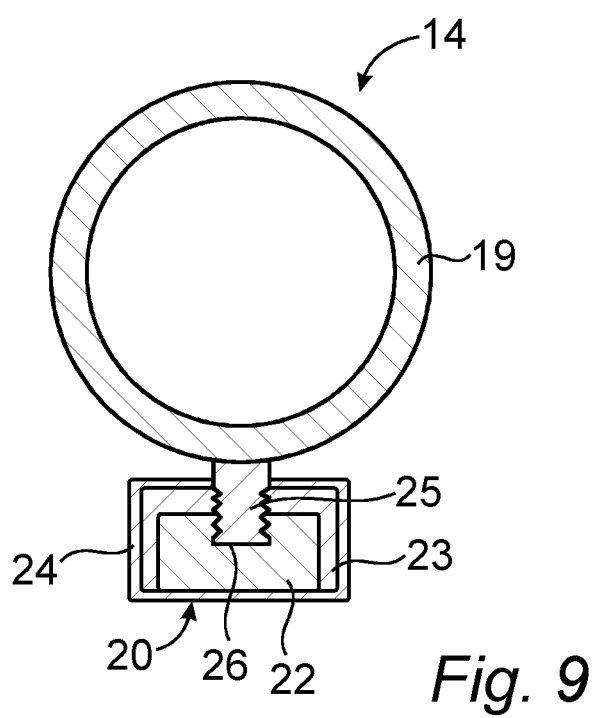

The invention will now be described more in detail with the aid of embodiments and with reference to the appended drawings, in which FIG. 1 is a schematic view from above of a system for positioning and restraining at least a part of a hand according to one embodiment, illustrating a support plate and a plurality of finger restraining elements, wherein a hand is positioned and restrained by means of the system, FIG. 2 is a schematic view from above of the system according to one embodiment, illustrating the support plate and the finger restraining elements, FIG. 3 is a schematic side view partially in section of the system according to one embodiment, wherein the support plate is provided with a drape and the finger restraining elements are positioned on the drape, FIG. 4 is a schematic perspective view of the finger restraining element according to one embodiment, FIG. 5 is a schematic view of a set of finger restraining elements according to one embodiment, FIG. 6 is a schematic section view of the finger restraining element according to one embodiment, illustrating a ring portion attached to a fastening portion of the finger restraining element, wherein the fastening portion comprises a casing and a partially covered magnet, FIG. 7 is a schematic section view of the finger restraining element according to another embodiment, wherein the magnet is entirely covered, FIG. 8 is a schematic section view of the finger restraining element according to another embodiment, wherein the magnet is enclosed by a first casing and a second casing, and FIG. 9 is a schematic section view of the finger restraining element according to another embodiment, wherein the ring portion is exchangeable.

THE INVENTION

With reference to FIGS. 1 and 2 a system 10 for positioning and restraining at least a part of a hand is illustrated according to one embodiment. The system 10 is arranged for positioning the hand 11 of a patient, or a part of the patient's hand, in a desired position and holding the hand 11, or part thereof, in the desired position, e.g. during a medical activity, such as hand surgery. The system 10 restraining the hand 11 is illustrated schematically in FIG. 1. According to one embodiment, the system 10 is a surgical restraining system, which also is called surgical fixing system, for restraining or fixing the hand 11 or part thereof during surgery of the hand 11. The hand 11 includes a palm side, a back side and a plurality of digits, which for a patient normally is five fingers 12, i.e. including the thumb 12a and four other fingers 12b-e. However, an injured or abnormal hand 11 can of course include another number of fingers 12, such as fewer fingers. For example, the system 10 is arranged for restraining the hand 11, or part thereof, when the hand 11 is subject to surgical treatment, such as invasive surgical treatment. For example, the system 10 is a surgical restraining system for orthopedic hand surgery or. In the following, positioning the hand, restraining the hand and similar expressions also casing the alternative of positioning part of the hand, restraining part of the hand, etc., unless otherwise is indicated. For example, the system 10 could be used for positioning and restraining only a specific part of the hand 11, such as one or more of the fingers 12, wherein the rest is left unrestrained. Alternatively, the system 10 is arranged for positioning and restraining the entire hand 11. Hence, the system 10 is arranged for use in surgical procedures when secure positioning of the hand or one or more of its fingers is desirable.

The system 10 comprises a support plate 13 and a plurality of finger restraining elements 14. The system 10 is arranged for receiving the hand 11 in the desired position on the support plate 13 through the finger restraining elements 14, wherein each of the finger restraining elements 14 is arranged to be connected to a finger 12 and to the support plate 13 to hold the hand 11 in the desired position on the support plate 13. Hence, the finger restraining elements 14 are connected to one or more of the fingers 12 and to the support plate 13 for fixing the hand 11 in relation to the support plate 13. In the illustrated embodiment, each of the finger restraining elements 14 is individually connectable to a finger 12, such as a single finger, and is individually connectable to the support plate 13. For example, each of the finger restraining elements 14 is individually and removably connectable to a finger 12 and is individually and detachably connectable to the support plate 13. Alternatively, one or more finger restraining elements 14 is/are connectable to a plurality of fingers 12, such as two or three fingers.

In FIG. 1 the hand 11 is illustrated with the back side (also called dorsal side) facing the support plate 13, e.g. for surgery in the palm side of the hand 11. Alternatively, the hand 11 is arranged with the palm side facing the support plate 13. Hence, the system 10 is arranged for positioning the hand 11 with any of the palm side and back side facing the support plate 13.

The support plate 13 comprises or is made of a magnetic material to which a magnet is attachable by magnetism. For example, the support plate 13 is made of a ferromagnetic material. For example, the support plate 13 comprises iron, nickel, cobalt or other metals, alloys and/or minerals to which a magnet is attachable by magnetism. The support plate 13 is arranged for supporting the finger restraining elements 14 connected to the hand 11. For example, the support plate 13 is substantially flat and extends in a single plane. For example, the support plate 13 is substantially rectangular or square, optionally with rounded corners. Alternatively, the support plate 13 is oval or circular. According to one embodiment, the support plate 13 is formed in a steel material to which a magnet is attachable by magnetism.

With reference also to FIG. 3, the support plate 13 has a front side 15 for carrying the finger restraining elements 14 and the hand 11, and a back side 16. For example, the front side 15 and the back side 16 are arranged substantially in parallel. In the embodiment of FIG. 3 the support plate 13, or at least the front side 15 thereof, is provided with a surgical drape 17 or equivalent enclosing. The drape 17 is removably arranged on the support plate 13, and is e.g. laid on top of the front side 15 of the support plate 13 before the surgery and before connecting the hand 11 to the support plate 13 by means of the finger restraining elements 14. For example, the drape 17 is arranged for enclosing also edges 18 of the support plate 13, and optionally also partially or entirely the back side 16 of the support plate 13. For example, the drape 17 is a conventional surgical drape.

A finger restraining element 14 according to one embodiment is illustrated more in detail in FIG. 4. The finger restraining element 14 comprises a ring portion 19 and a fastening portion 20. For example, the finger restraining element 14 comprises a single ring portion 19. Alternatively, the finger restraining element 14 comprises a plurality of ring portions, which is not illustrated in the drawings. The ring portion 19 is arranged for receiving a finger 12, such as a single finger, to connect the finger restraining element 14 to the finger 12. Hence, the ring portion 19 is arranged for removably connecting the finger restraining element 14 to the finger 12, wherein the finger restraining element 14 is removably connectable to the finger 12. The ring portion 19 is attached to the fastening portion 20. For example, the ring portion 19 is fixed to the fastening portion 20. For example, the ring portion 19 is integrated with the fastening portion 20. Alternatively, the ring portion 19 is detachably attached to the fastening portion 20 and is exchangeable, which is described more in detail below. For example, the ring portion 19 is arranged as a closed loop, wherein the finger 12 can be introduced into the ring portion 19. The ring portion 19 is rigid. For example, the ring portion 19 is made of metal, such as stainless steel, titanium, aluminum or another suitable metal or alloy. Alternatively, the ring portion 19 is made of a plastic material or a composite material.

With reference to FIG. 5 a set of finger restraining elements 14 is disclosed according to one example. According to one embodiment the system 10 comprises at least one set 21 of finger restraining elements 14, wherein said set 21 includes at least a first finger restraining element 14a and a second finger restraining element 14b having a ring portion 19 of a different size than the ring portion 19 of the first finger restraining element 14a to fit fingers of different sizes. Hence, the ring portions 19 are arranged with an inner diameter D, wherein the inner diameter D of the first finger restraining element 14a is different from the inner diameter D of the second restraining element 14b. For example, the set 21 comprises five finger restraining elements 14a-e. According to one embodiment, the set 21 comprises finger restraining elements 14 having ring portions 19 of at least three different sizes. For example, the system 10 comprises a plurality of different sets 21 of finger restraining elements 14 to fit different fingers 11 of the hand 11 and to fit different hands 11. For example, a first set 21 of finger restraining elements 14 is arranged for fitting a hand of a first size, wherein a second set of finger restraining elements 14 is arranged for fitting a hand of a second size different from the first size.

With reference to FIG. 6 the finger restraining element 14 is illustrated according to one embodiment, wherein the ring portion 19 is fixed to or integral with the fastening portion 20. The fastening portion 20 comprises a permanent magnet 22 for fastening of the finger restraining element 14 to the support plate 13. For example, the magnet 22 is arranged for fastening the finger restraining element 14 to the support plate 13 through the drape 17, wherein the drape 17 is arranged between the support plate 13 and the fastening portion 20. Hence, the fastening portion 20 is arranged for detachably fastening of the finger restraining element 14 to the support plate 13 by magnetism to secure the hand 11 in a satisfactorily manner during the medical activity and prevent unintentional displacement of the hand 11 during such activity while allowing manual positioning and repositioning of the finger restraining element 14 on the support plate 13. The finger restraining element 14 comprises the fastening portion 20, wherein the finger restraining element 14 is detachably attachable to the support plate 13 by means of magnetism through the permanent magnet 22 of the fastening portion 20. The permanent magnet 22 comprises a magnetic material, such as iron, cobalt, nickel, neodymium or other metals, alloys or minerals or combinations thereof that can be magnetized to produce a magnetic field for attachment to the support plate 13 by magnetic forces. According to one embodiment the magnet 22 is a neodymium magnet, i.e. the magnet comprises neodymium. For example, the magnet 22 comprises neodymium, iron and boron. Alternatively, the magnet 22 comprises other metals for producing strong permanent magnets.

For example, the magnet 22 comprises zirconium. According to one embodiment, the magnet 22 is heat resistant and tolerates an operational temperature of at least 120 degrees without irreversible demagnetization. For example, the magnet 22 can be sterilized, e.g. in an autoclave, without irreversible demagnetization. For example, the magnet 22 is a neodymium magnet of grade N28EH-N35EH. According to one embodiment, the permanent magnet 22 is arranged with a top side and a bottom side, wherein the front and back sides are connected by one or more vertically extending walls. In the illustrated embodiment, the top and bottom sides are substantially plane and level and are arranged substantially in parallel. In the illustrated embodiment, the permanent magnet 22 is circular. Alternatively, the permanent magnet 22 is of any suitable shape, such as rectangular, oval, square, etc.

The magnet 22 is at least partially enclosed by a casing 23. The casing 23 encloses at least the vertically extending wall, e.g. around the entire periphery of the magnet 22. In the embodiment of FIG. 6, the casing 23 encloses the top side and the vertically extending wall of the magnet 22. Hence, the bottom side of the magnet 22 is not covered by the casing 23. The magnet 22 is attached to the casing 23, such as by means of an adhesive or by other conventional fastening means. For example, the magnet 22 is fixed to the casing 23. According to one embodiment, the casing 23 is arranged in a magnetic material, such as a magnetic steel material, wherein the magnet 22 and the casing 23 together form a so called magnetic system to enhance the magnetic strength and direct the magnetic field downward toward the support plate 13. According to one embodiment, the casing 23 is arranged in a material that can be sterilized, e.g. by means of a conventional autoclave or similar. The ring portion 19 is, e.g. attached to the casing 23 of the fastening portion 20.

With reference to FIG. 7, the finger restraining element 14 is illustrated according to one alternative embodiment, wherein the fastening portion 20 comprises a cover 24 enclosing the magnet 22. In the embodiment of FIG. 7 the magnet 22 is entirely enclosed by the cover 24. Alternatively, the ring portion 19 and the cover 24 together encloses the magnet 22 entirely. The cover 24 is, for example, made of a material the can be sterilized, e.g. by means of a conventional autoclave or similar. In the embodiment of FIG. 7, the ring portion 19 is attached to the cover 24 of the fastening portion 20. For example, the cover 24 is arranged in stainless steel, such as a non-magnetic stainless steel. For example, the cover is made of a material not having ferromagnetic properties. Alternatively, the cover 24 is made in titanium, aluminum or any other suitable metal or of composite materials or plastic materials. For example, the cover 24 and the ring portion 19 are integrated to form a single unit and are, for example, formed in the same material. For example, the finger restraining elements 14 are arranged with smooth and even surfaces for comfortable handling and to facilitate cleaning.

With reference to FIG. 8 the finger restraining element 14 is illustrated according to another embodiment, wherein the fastening portion 20 comprises the casing 23 and the cover 24 enclosing the magnet 22. In the embodiment of FIG. 8 the magnet 22 is partially enclosed by the casing 23, wherein the casing 23 and magnet 22 are entirely enclosed by the cover 24. Alternatively, the casing 23 and magnet 22 are partially enclosed by the cover 24, wherein the cover 24, e.g. encloses the bottom side of the magnet 22 and one or more vertically extending walls of the casing 23. In FIG. 8, the casing 23 encloses at least the vertically extending wall of the magnet, such as the top side and the vertically extending wall of the magnet 22. For example, the casing 23 engages the magnet 22. The casing 23 is arranged between the side walls of the magnet 22 and the cover 24. The cover 24 engages the bottom side of the magnet 22 and at least a vertically extending wall of the casing 23, such as a top side and the vertically extending wall of the casing 23. For example, the casing 23 is arranged in a magnetic material as described with reference to FIG. 6. For example, the cover is arranged in a nonmagnetic material as described with reference to FIG. 7.

With reference to FIG. 9 the finger restraining element 14 is illustrated schematically according to another embodiment, wherein the ring portion 19 is detachably connectable to the fastening portion 20 to form a module system in which different ring portions 19 can be attached to the fastening portion 20. Hence, the ring portion 19 is exchangeable, so that the fastening portion 20 with the magnet 22 can be used for different ring portions 19 having different inner diameters D to fit different finger sizes or different patients. For example, the ring portion 19 is connectable to the fastening portion through mechanical fastening means, such as conventional mechanical fastening means, such as a threaded connection, bayonet mount or another type of suitable connection. In the embodiment of FIG. 8, the ring portion 19 is provided with a screw 25, and the fastening portion 20 is provided with a threaded hole 26 for receiving the screw 25. For example, the hole 26 extends from a top side of the fastening portion 20 and extends substantially vertically downward, such as through the cover 24 and through the casing 23 and into the magnet 22. Alternatively, the fastening portion 20 is provided with a screw, e.g. extending upward, to be received in a threaded hole in the ring portion 19. For example, the ring portion 19 is forged in stainless steel. Alternatively, the ring portion 19 arranged in titanium, aluminum or other suitable metal or composite or plastic materials. Such a module system comprises one or more fastening portions 20 and a plurality of ring portions 19. For example, the module system comprises a set of fastening portions 20 and a plurality of sets 21 of ring portions 19.

The invention claimed is:

1. A surgical fixing system for positioning and restraining at least a part of a hand, comprising a support plate and a plurality of finger restraining elements, wherein each of the finger restraining elements is removably connectable to a finger or a plurality of fingers, and is detachably attachable to the support plate, wherein
the support plate comprises a magnetic material, and wherein each of the finger restraining elements comprises a rigid closed loop ring portion for receiving a finger and enclosing a circumference thereof, and a fastening portion that is in contact with the support plate and that has a permanent magnet for attaching the finger restraining element to the support plate, so that when a finger is received in the ring portion the finger is secured to the support plate in a desired position, the permanent magnet configured to direct a magnetic field toward the support plate such that the fastening portion is magnetically urged toward the support plate.

2. The surgical fixing system according to claim 1, wherein a cover encloses the magnet.

3. The surgical fixing system according to claim 2, wherein the cover is arranged in a non-magnetic material.

4. The surgical fixing system according to claim 3, wherein the cover and the ring portion form a single integrated unit in the same non-magnetic material.

5. The surgical fixing system according to claim 2, wherein the fastening portion comprises a casing at least partially enclosing the permanent magnet and the cover encloses the casing and the permanent magnet.

6. The surgical fixing system according to claim 1, wherein the fastening portion comprises a casing at least partially enclosing the permanent magnet.

7. The surgical fixing system according to claim 6, wherein the casing extends around a periphery of the permanent magnet between a top side and a bottom side thereof.

8. The surgical fixing system according to claim 6, wherein the casing is formed in a magnetic material.

9. The surgical fixing system according to claim 1, wherein the ring portion arranged with an inner diameter (D) of at least 18 mm.

10. The surgical fixing system according to claim 9, wherein the inner diameter (D) of the ring portion is 18 mm to 28 mm.

11. The surgical fixing system according to claim 1, comprising a first finger restraining element having a ring portion arranged with an inner first diameter (D), and a second finger restraining element having a ring portion arranged with an inner second diameter, wherein the inner first diameter differs from the inner second diameter.

12. The surgical fixing system according to claim 11, comprising a first set of finger restraining elements having ring portions of different inner diameters (D), and a second set of restraining elements having ring portions of different inner diameters (D), wherein the first set is different from the second set.

13. The surgical fixing system according to claim 1, wherein the ring portion has a circular opening.

14. The surgical fixing system according to claim 1, wherein the permanent magnet is a magnet tolerating an operational temperature of at least 120 degrees C.

15. The surgical fixing system according to claim 1, wherein the support plate is covered by a removable surgical drape, and wherein the fastening portion is arranged for attaching the finger restraining element to the support plate through the surgical drape.

16. The surgical fixing system according to claim 1, wherein the ring portion is fixed to the fastening portion.

* * * * *